(12) United States Patent
Kovach et al.

(10) Patent No.: US 9,510,935 B2
(45) Date of Patent: *Dec. 6, 2016

(54) ARTICLES INCLUDING EXPANDED POLYTETRAFLUOROETHYLENE MEMBRANES WITH SERPENTINE FIBRILS AND HAVING A DISCONTINUOUS FLUOROPOLYMER LAYER THEREON

(71) Applicant: W. L. Gore & Associates, Inc., Newark, DE (US)

(72) Inventors: Larry J Kovach, Flagstaff, AZ (US); Rachel Radspinner, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 105 days.

This patent is subject to a terminal disclaimer.

(21) Appl. No.: 13/675,730

(22) Filed: Nov. 13, 2012

(65) Prior Publication Data

US 2013/0184807 A1     Jul. 18, 2013

Related U.S. Application Data

(63) Continuation-in-part of application No. 13/351,052, filed on Jan. 16, 2012, now abandoned.

(51) Int. Cl.
*A61F 2/07* (2013.01)
*C09D 127/18* (2006.01)
(Continued)

(52) U.S. Cl.
CPC . *A61F 2/07* (2013.01); *A61F 2/82* (2013.01); *A61L 31/048* (2013.01); *A61L 31/10* (2013.01);
(Continued)

(58) Field of Classification Search
CPC ....... A61F 2/82; A61F 2/91; A61F 2250/0098
(Continued)

(56) References Cited

U.S. PATENT DOCUMENTS 3,953,566 A *   4/1976  Gore ............................ 264/505
4,877,661 A    10/1989  House et al.
(Continued)

FOREIGN PATENT DOCUMENTS

EP    0 293 090    11/1988
EP    0 815 806     1/1997
(Continued)

OTHER PUBLICATIONS

International Search Report and Written Opinion for PCT/US2012/064908 mailed Feb. 4, 2013, corresponding to U.S. Appl. No. 13/675,730, 11 pages.
(Continued)

*Primary Examiner* — Jason-Dennis Stewart
(74) *Attorney, Agent, or Firm* — Amy L. Miller

(57) ABSTRACT

Articles comprising an expanded polytetrafluoroethylene membrane having serpentine fibrils and having a discontinuous coating of a fluoropolymer thereon are provided. The fluoropolymer may be located at least partially in the pores of the expanded fluoropolymer membrane. In exemplary embodiments, the fluoropolymer is fluorinated ethylene propylene. The application of a tensile force at least partially straightens the serpentine fibrils, thereby elongating the article. The expanded polytetrafluoroethylene membrane may include a microstructure of substantially only fibrils. The articles can be elongated to a predetermined point at which further elongation is inhibited by a dramatic increase in stiffness. In one embodiment, the articles are used to form a covered stent device that requires little force to distend in the radial direction to a first diameter but is highly resistant
(Continued)

to further distension to a second diameter (stop point). A large increase in diameter can advantageously be achieved prior to reaching the stop point.

35 Claims, 4 Drawing Sheets

(51) Int. Cl.
| | |
|---|---|
| *B32B 38/18* | (2006.01) |
| *A61F 2/82* | (2013.01) |
| *F21V 33/00* | (2006.01) |
| *A61L 31/10* | (2006.01) |
| *A61L 31/12* | (2006.01) |
| *A61L 31/14* | (2006.01) |
| *A61L 31/04* | (2006.01) |

(52) U.S. Cl.
CPC ............ *A61L 31/129* (2013.01); *A61L 31/146* (2013.01); *B32B 38/1866* (2013.01); *C09D 127/18* (2013.01); *F21V 33/0076* (2013.01); *A61F 2002/075* (2013.01); *Y10T 156/1075* (2015.01); *Y10T 428/2481* (2015.01); *Y10T 428/24802* (2015.01)

(58) Field of Classification Search
USPC ...................................... 623/1.15, 1.34, 1.13
See application file for complete search history.

(56) References Cited

U.S. PATENT DOCUMENTS

| | | | |
|---|---|---|---|
| 5,026,513 | A | 6/1991 | House et al. |
| 5,071,609 | A | 12/1991 | Tu et al. |
| 5,476,589 | A | 12/1995 | Bacino |
| 5,534,007 | A | 7/1996 | St. Germain et al. |
| 5,549,663 | A | 8/1996 | Cottone |
| 5,708,044 | A | 1/1998 | Branca |
| 5,718,973 | A * | 2/1998 | Lewis et al. ................. 623/1.32 |
| 5,759,192 | A | 6/1998 | Saunders |
| 5,769,884 | A | 6/1998 | Solovay |
| 5,772,884 | A | 6/1998 | Tanaka et al. |
| 5,824,043 | A | 10/1998 | Cottone |
| 5,843,158 | A | 12/1998 | Lenker et al. |
| 5,843,161 | A | 12/1998 | Solovay |
| 5,935,162 | A | 8/1999 | Dang |
| 6,010,529 | A | 1/2000 | Herweck et al. |
| 6,013,854 | A | 1/2000 | Moriuchi |
| 6,042,588 | A | 3/2000 | Munsinger et al. |
| 6,042,606 | A | 3/2000 | Frantzen |
| 6,190,406 | B1 | 2/2001 | Duerig et al. |
| 6,245,012 | B1 | 6/2001 | Kleshinski |
| 6,245,939 | B1 | 6/2001 | Hsu |
| 6,261,320 | B1 | 7/2001 | Tam et al. |
| 6,261,620 | B1 | 7/2001 | Leadbetter |
| 6,436,132 | B1 | 8/2002 | Patel et al. |
| 6,488,701 | B1 | 12/2002 | Nolting et al. |
| 6,541,589 | B1 | 4/2003 | Baillie |
| 6,620,190 | B1 | 9/2003 | Colone |
| 6,626,939 | B1 | 9/2003 | Burnside et al. |
| 6,730,120 | B2 | 5/2004 | Berg et al. |
| 6,755,856 | B2 | 6/2004 | Fierens et al. |
| 6,758,858 | B2 | 7/2004 | McCrea et al. |
| 7,049,380 | B1 | 5/2006 | Chang et al. |
| 7,083,642 | B2 | 8/2006 | Sirhan et al. |
| 7,105,018 | B1 | 9/2006 | Yip et al. |
| 7,306,729 | B2 | 12/2007 | Bacino et al. |
| 7,419,678 | B2 | 9/2008 | Falotico |
| 7,531,611 | B2 | 5/2009 | Sabol et al. |
| 7,789,908 | B2 | 9/2010 | Sowinski et al. |
| 7,811,314 | B2 | 10/2010 | Fierens et al. |
| 7,815,763 | B2 | 10/2010 | Fierens et al. |
| 7,927,364 | B2 | 4/2011 | Fierens et al. |
| 7,927,365 | B2 | 4/2011 | Fierens et al. |
| 7,935,141 | B2 | 5/2011 | Randall et al. |
| 7,967,829 | B2 | 6/2011 | Gunderson et al. |
| 2002/0198588 | A1 | 12/2002 | Armstrong et al. |
| 2003/0060871 | A1 | 3/2003 | Hill et al. |
| 2004/0024448 | A1 | 2/2004 | Chang |
| 2005/0080476 | A1 | 4/2005 | Gunderson et al. |
| 2005/0283224 | A1 | 12/2005 | King |
| 2006/0036311 | A1 | 2/2006 | Nakayama et al. |
| 2006/0259133 | A1 * | 11/2006 | Sowinski et al. ............ 623/1.54 |
| 2006/0276883 | A1 | 12/2006 | Greenberg et al. |
| 2007/0012624 | A1 | 1/2007 | Bacino et al. |
| 2007/0060999 | A1 | 3/2007 | Randall et al. |
| 2007/0129786 | A1 | 6/2007 | Beach et al. |
| 2007/0207186 | A1 * | 9/2007 | Scanlon .................... A61F 2/07 424/424 |
| 2007/0208421 | A1 | 9/2007 | Quigley |
| 2007/0213800 | A1 | 9/2007 | Fierens et al. |
| 2007/0250146 | A1 | 10/2007 | Cully et al. |
| 2007/0250153 | A1 | 10/2007 | Cully et al. |
| 2007/0254012 | A1 | 11/2007 | Ludwig et al. |
| 2008/0051876 | A1 | 2/2008 | Ta et al. |
| 2008/0119943 | A1 | 5/2008 | Armstrong et al. |
| 2008/0319531 | A1 | 12/2008 | Doran et al. |
| 2009/0005854 | A1 | 1/2009 | Huang et al. |
| 2009/0030499 | A1 * | 1/2009 | Bebb et al. .................. 623/1.13 |
| 2009/0043373 | A1 | 2/2009 | Arnault de la Menardiere et al. |
| 2009/0182413 | A1 | 7/2009 | Burkart et al. |
| 2010/0094394 | A1 | 4/2010 | Beach et al. |
| 2010/0094405 | A1 | 4/2010 | Cottone |
| 2010/0106240 | A1 | 4/2010 | Duggal et al. |
| 2010/0159171 | A1 | 6/2010 | Cough |
| 2013/0184807 | A1 | 7/2013 | Kovach et al. |
| 2014/0135897 | A1 | 5/2014 | Cully et al. |
| 2014/0172066 | A1 | 6/2014 | Goepfrich et al. |
| 2014/0180402 | A1 | 6/2014 | Bruchman et al. |

FOREIGN PATENT DOCUMENTS

| | | |
|---|---|---|
| EP | 0 893 108 | 1/1999 |
| JP | H02000645 | 1/1990 |
| JP | H09-501759 | 2/1997 |
| JP | H09-241412 | 9/1997 |
| JP | H11-290448 | 10/1999 |
| JP | 2005-530549 | 10/2005 |
| JP | 2008-506459 | 3/2008 |
| RU | 20124986 | 8/1994 |
| WO | 95/05555 | 2/1995 |
| WO | 97/10871 | 3/1997 |
| WO | 00/41649 | 7/2000 |
| WO | 01/74272 | 10/2001 |
| WO | WO 02/060506 | 8/2002 |
| WO | WO 04/000375 | 12/2003 |
| WO | 2008/028964 | 3/2008 |
| WO | 2008/036870 | 3/2008 |
| WO | 2008/049045 | 4/2008 |
| WO | 2009/100210 | 8/2009 |
| WO | 2010/006783 | 1/2010 |
| WO | 2010/030766 | 3/2010 |
| WO | 2010/132707 | 11/2010 |

OTHER PUBLICATIONS

International Search Report and Written Opinion for PCT/US2012/066518, mailed Feb. 4, 2013, corresponding to U.S. Appl. No. 13/351,052, 12 pages.
Partial International Search Report for PCT/US2012/065066, Jul. 1, 2013, 3 pages.
International Search Report and Written Opinion for PCT/US2011/061165 mailed Oct. 1, 2012, corresponding to U.S. Appl. No. 13/298,060.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

(56) References Cited

OTHER PUBLICATIONS

International Search Report and Written Opinion for PCT/US2012/064910 mailed Feb. 1, 2013, corresponding to U.S. Appl. No. 13/675,764, 8 pages.
Google Image Search Results, "S-Shaped", accessed Nov. 2, 2013.

\* cited by examiner

ARTICLES INCLUDING EXPANDED POLYTETRAFLUOROETHYLENE MEMBRANES WITH SERPENTINE FIBRILS AND HAVING A DISCONTINUOUS FLUOROPOLYMER LAYER THEREON

FIELD OF THE INVENTION

The present invention relates to expanded polytetrafluoroethylene (ePTFE) membranes having serpentine fibrils and a discontinuous fluoropolymer layer and to materials made therefrom.

DEFINITIONS

As used herein, the term "serpentine fibrils" means multiple fibrils that curve or turn one way then another.

As used herein, the term "controlled retraction" refers to causing articles to shorten in length in at least one direction by the application of heat, by wetting with a solvent, or by any other suitable means or combinations thereof in such a way as to inhibit folding, pleating, or wrinkling of the subsequent article visible to the naked eye.

The term "imbibed or imbibing" as used herein is meant to describe any means for at least partially filling at least a portion of the pores of a porous material such as ePTFE or the like.

The term "elongation" as used herein is meant to denote the increase in length in response to the application of a tensile force.

The term "discontinuously located" as used herein refers to a substance having at least one unconnected region.

The term "precursor membrane" as used herein refers to the starting membrane.

The terms "stent graft" and "covered stent" may be used interchangeably herein to describe a stent with a cover thereon.

The term "increase in stiffness" as used herein refers the increase in resistance to further elongation once the stoppoint is reached.

For purposes of this invention, the entire device is considered to be "wrinkle-free" if within a 1 cm length of the device, the graft portion is devoid of wrinkles and folds. It is to be noted that the terms "free of folds", "devoid of folds", and "fold free" are used interchangeably herein.

BACKGROUND OF THE INVENTION

Porous fluoropolymer materials, and in particular, expanded polytetrafluoroethylene (ePTFE) materials, typically exhibit relatively low elongation when stressed in the direction parallel to the orientation of the fibrils. High strength ePTFE materials have relatively low elongation values compared to lower strength ePTFE materials. Uniaxially expanded materials can exhibit high elongation when stressed in the direction orthogonal to the fibrils; however, the membranes are exceptionally weak in this direction.

Uniaxially expanded ePTFE tubes positioned on mandrels have been mechanically compressed and heat treated to achieve higher elongations prior to rupture. Such tubes also exhibit recovery if elongated prior to rupture and released from stress. U.S. Pat. No. 4,877,661 to House, et al. discloses porous PTFE having the property of rapid recovery and a method for producing these materials. Additionally, the pores of compressed tubes have been penetrated with elastomeric materials. For example, U.S. Pat. No. 7,789,908 to Sowinski, et al. discloses an elastomeric recoverable PTFE material that includes longitudinally compressed fibrils of an ePTFE material penetrated by an elastomeric material within the pores which define an elastomeric matrix.

A need continues to exist for thin, strong membranes that exhibit high degrees of elongation, such as greater than 50% elongation. Some applications further demand qualities such as thinness, low density, and/or small pore size, as well as combinations thereof. Other applications require a relatively low force to elongate the membrane.

SUMMARY OF THE INVENTION

The present invention is directed to fluoropolymer membranes that exhibit high elongation while substantially retaining the strength properties of the fluoropolymer membrane. Such membranes characteristically possess serpentine fibrils having a width of about 1.0 micron or less.

It is an object of the present invention to provide an article that includes an expanded fluoropolymer membrane having a discontinuous coating of a fluoropolymer thereon. The fluoropolymer may be located at least partially in some or all of the pores of the expanded fluoropolymer membrane. The expanded fluoropolymer membrane characteristically contains serpentine fibrils, and may have a microstructure of substantially only serpentine fibrils. The serpentine fibrils have a width less than about 1.0 micron or less. In one exemplary embodiment, the expanded fluoropolymer membrane includes a plurality of serpentine fibrils. In at least one embodiment of the invention, the fluoropolymer membrane is expanded polytetrafluoroethylene. One exemplary fluoropolymer is fluorinated ethylene propylene. The application of a tensile force at least partially straightens the serpentine fibrils, thereby elongating the article. The composite material exhibits high elongation while substantially retaining the strength properties of the fluoropolymer membrane. Additionally, the expanded fluoropolymer membrane may be thermally retracted in at least one direction to less than about 90% of the initial, expanded fluoropolymer length. Also, the expanded fluoropolymer membrane may be restrained in at least one direction during the thermal retraction.

It is another object of the present invention to provide an endoprosthetic device that includes a tubular member defining at least one opening, an interior surface, and an exterior surface where the tubular member includes a composite material including a fluoropolymer membrane having serpentine fibrils and a discontinuous coating of a fluoropolymer. The serpentine fibrils have a width less than about 1.0 micron or less. The fluoropolymer may be located at least partially in some or all of the pores of the expanded fluoropolymer membrane. In one or more exemplary embodiment, the fluoropolymer membrane includes expanded polytetrafluoroethylene and the fluoropolymer includes fluorinated ethylene propylene. The composite material exhibits an increase in stiffness when expanded to a diameter of about 7 mm. The tubular member may be used as a covering for a stent.

It is a further object of the present invention to provide a stent graft that includes (1) a stent having a wall with at least one opening, an exterior surface, and an interior surface and (2) a cover affixed to the stent where the cover includes a composite material including an expanded polytetrafluoroethylene membrane having serpentine fibrils and a discontinuous coating of a fluoropolymer. The fluoropolymer may be located at least partially in all or substantially all of the pores of the expanded fluoropolymer membrane. The serpentine fibrils have a width of about 1.0 micron or less. The composite material at least partially covers at least one of the interior and exterior surfaces of the stent. In addition, the composite material may be affixed to the exterior and/or interior surface of the stent. The fluoropolymer may be fluorinated ethylene propylene. The composite material remains wrinkle-free and fold-free regardless of the diameter of the stent graft. Also, the composite material exhibits high elongation while substantially retaining the strength properties of the polytetrafluoroethylene membrane. The expanded polytetrafluoroethylene membrane may include a microstructure of substantially only serpentine fibrils. In one embodiment, the expanded fluoropolymer membrane may include a plurality of serpentine fibrils. The composite material exhibits an increase in stiffness when expanded to a diameter of about 7 mm.

It is also an object of the present invention to provide a stent graft having (1) a wall with at least one opening, an exterior surface, and an interior surface and (2) a cover affixed to the stent where the cover includes a composite material including an expanded fluoropolymer membrane and a discontinuous coating of a fluoropolymer thereon. The composite material exhibits an increase in stiffness when expanded to a diameter of about 7 mm. Additionally, the composite material at least partially covers at least one of the interior and exterior surfaces of the stent. It is to be appreciated that the fluoropolymer is not substantially adhered to the stent. The fluoropolymer may be fluorinated ethylene propylene. The expanded polytetrafluoroethylene membrane may include a microstructure of substantially only serpentine fibrils. In at least one exemplary embodiment, the expanded fluoropolymer membrane may include a plurality of serpentine fibrils.

It is yet another object of the present invention to provide a method of forming a covered stent that includes (1) positioning a first tubular member on an interior surface of a stent, (2) positioning a second tubular member on an external surface of the stent, where each tubular member includes a composite material having an expanded polytetrafluoroethylene membrane and a discontinuous coating of a fluoropolymer thereon and the expanded polytetrafluoroethylene membrane includes serpentine fibrils, and (3) heating the stent having thereon the first and second tubular members to adhere the fluoropolymer on the first tubular member to the second tubular member through interstices of the stent and form a covered stent. The fluoropolymer is positioned on an external surface of the first tubular member and on an interior surface of the second tubular member. The serpentine fibrils have a width of about 1.0 micron or less. In at least one embodiment, the fluoropolymer is fluorinated ethylene propylene.

It is a further object of the present invention to provide a method of forming a covered stent that includes (1) forming a tube having a composite material that includes an expanded polytetrafluoroethylene membrane and a discontinuous coating of a fluoropolymer thereon, where the fluoropolymer is positioned on an external surface of the tube, (2) cutting the tube cross-sectionally to form a first tubular member and a second tubular member, (3) everting the second tubular member to position the fluoropolymer on an interior surface of the second tubular member, (4) positioning the first tubular member within a stent, (5) positioning the second tubular member on an external surface of the stent, and (6) heating the stent having thereon the first and second tubular members to adhere the fluoropolymer on the first tubular member to the second tubular member through interstices of the stent to form a covered stent. In exemplary embodiments, the expanded fluoropolymer membrane includes serpentine fibrils. The serpentine fibrils have a width of about 1.0 micron or less.

The foregoing and other objects, features, and advantages of the invention will appear more fully hereinafter from a consideration of the detailed description that follows. It is to be expressly understood, however, that the drawings are for illustrative purposes and are not to be construed as defining the limits of the invention.

BRIEF DESCRIPTION OF THE FIGURES

The advantages of this invention will be apparent upon consideration of the following detailed disclosure of the invention, especially when taken in conjunction with the accompanying drawings wherein.

DETAILED DESCRIPTION OF THE INVENTION

Figure 1:
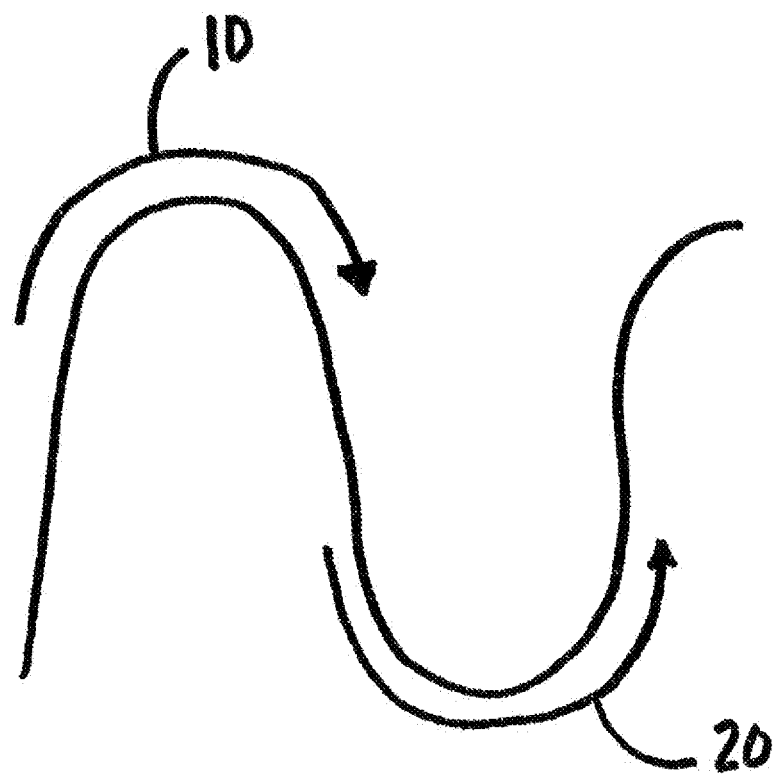
FIG. 1 is a schematic illustration of an exemplary, idealized serpentine fibril.

Unless defined otherwise, all technical and scientific terms used herein have the same meaning as commonly understood by one of ordinary skill in the art to which the invention belongs. In the drawings, the thickness of the lines, layers, and regions may be exaggerated for clarity. Like numbers found throughout the figures denote like elements.

The present invention is directed to fluoropolymer membranes that exhibit high elongation while substantially retaining the strength properties of the fluoropolymer membrane. Such membranes characteristically possess serpentine fibrils, such as the idealized serpentine fibril exemplified in FIG. 1. As depicted generally in FIG. 1, a serpentine fibril curves or turns generally one way in the direction of arrow 10 then generally another way in the direction of arrow 20. It is to be understood that the amplitude, frequency, or periodicity of the serpentine-like fibrils as exemplified in FIG. 1 may vary. In one embodiment, the fluoropolymer membranes are expanded fluoropolymer membranes. Non-limiting examples of expandable fluoropolymers include, but are not limited to, expanded PTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabot et al.; U.S. patent application Ser. No. 11/906,877 to Ford; and U.S. patent application Ser. No. 12/410,050 to Xu et al.

The high elongation is enabled by forming relatively straight fibrils into serpentine fibrils that substantially straighten upon the application of a force in a direction opposite to the compressed direction. The creation of the serpentine fibrils can be achieved through a thermally-induced controlled retraction of the expanded polytetrafluoroethylene, through wetting the article with a solvent (followed by drying), or by a combination of these two techniques. The solvent may be, but is not limited to, isopropyl alcohol or Fluorinert® (a perfluorinated solvent commercially available from 3M, Inc., St. Paul, Minn.). In general, for unrestrained articles, the higher the temperature and the longer the dwell time, the higher the degree of retraction up to the point of maximum retraction. In addition, the speed of retraction can be increased by increasing the retraction temperature. The retraction of the membrane does not result in visible pleating, folding, or wrinkling of the ePTFE, unlike what occurs during mechanical compression. The retraction also can be applied to very thin membranes, unlike known methods. During the retraction process, the fibrils become serpentine in shape and, in some instances, may also increase in width.

The precursor materials can be biaxially expanded ePTFE membranes. In one embodiment, materials such as those made in accordance with the general teachings of U.S. Pat. No. 7,306,729 to Bacino, et al. are suitable precursor membranes, especially if small pore size articles are desired. These membranes may possess a microstructure of substantially only fibrils. The precursor membrane may or may not be amorphously locked. Additionally, the precursor membrane may be at least partially filled, coated, imbibed, or otherwise combined with additional materials. For example, the precursor membrane may contain or be at least partially coated or imbibed with a fluoropolymer, such as, for example, fluorinated ethylene propylene.

The precursor membrane may be restrained in one or more directions during the retraction process in order to prescribe the desired amount of elongation of the final article. The amount of elongation is directly related to, and is determined by, the amount of retraction. In the instant invention, the amount of retraction can be less than about 90%, 75%, 50%, or 25% of the initial un-retracted length. The resultant amounts of elongation in the direction of retraction can be at least about 60%, 80%, 100%, 200%, 300%, 400%, 500%, 600%, or even greater, including any and all percentages therebetween.

The retraction temperature range includes temperatures that result in the retraction of the precursor membrane. In some instances, the retraction temperature can exceed the amorphous locking temperature of the precursor membrane.

In one embodiment, retraction can be achieved in a uniaxial tenter frame by positioning the rails at a distance less than the width of the precursor membrane prior or during the application of heat or solvent or both. When using a biaxial tenter frame, one or both of the sets of grips, pins, or other suitable attachment means can similarly be positioned at a distance less than the dimensions of the precursor membrane. It is to be appreciated that these retraction means differ from the mechanical compression taught by the House and Sowinski patents noted above.

In another embodiment, the article can be retracted while being held by hand. A tubular article can be retracted by fitting it over a mandrel prior to retraction. In yet another embodiment, the membrane can be placed in an oven and allowed to retract unrestrained. It is to be understood that any suitable means of retracting the article that does not result in the formation of visible folds, pleats, or wrinkles can be employed.

The resulting retracted articles surprisingly exhibit high elongation while substantially retaining the strength properties of the fluoropolymer membrane. Upon retraction, the expanded fluoropolymer membrane possesses serpentine fibrils. These retracted membranes characteristically possess serpentine fibrils and are free of wrinkles. In some exemplary embodiments, the retracted membranes may possess a microstructure of substantially only serpentine fibrils. In certain instances, it may be necessary to partially elongate the retracted membrane in order to observe the serpentine fibrils with magnification. In at least one embodiment, the fluoropolymer membranes include a plurality of serpentine fibrils. As used herein, the phrase "plurality of serpentine fibrils" is meant to denote the presence of 2 or more, 5 or more, 10 or more, or 15 or more serpentine fibrils in the fluoropolymer membrane within a field of view as taught below. The serpentine fibrils have a width of about 1.0 micron or less, and in some embodiments, about 0.5 microns or less. In one embodiment, the serpentine fibrils have a width from about 0.1 to about 1.0 microns, or from about 0.1 to about 0.5 microns.

In another embodiment of the present invention, the precursor membranes described above can be imbibed with an elastomeric material prior, during, or subsequent to retraction to form a composite material. In the absence of such elastomeric materials, fluoropolymer articles having serpentine fibrils do not exhibit appreciable recovery after elongation. Suitable elastomeric materials include, but are not limited to, PMVE-TFE (perfluoromethylvinyl ether-tetrafluoroethylene) copolymers, PAVE-TFE (perfluoro (alkyl vinyl ether)tetrafluoroethylene) copolymers, silicones, polyurethanes, and the like. It is to be noted that PMVE-TFE and PAVE-TFE are fluoroelastomers. Other fluaroelastomers are suitable elastomeric materials. The resultant retracted article not only possesses high elongation while substantially retaining the strength properties of the fluoropolymer membrane, but also possesses the additional property of low percent unrecoverable strain energy density. These articles can exhibit percent unrecoverable strain energy density values less than about 85%, less than about 80%, less than about 70%, less than about 60%, and lower, including any and all percentages therebetween.

In another embodiment of the invention, the precursor membrane is imbibed or coated, at least partially or completely, or otherwise combined with at least one other material that may include, but is not limited to, fluorinated ethylene propylene (FEP), other fluoropolymers, polymers, copolymers, or terpolymers, ethylene fluorinated ethylene propylene (EFEP), THV (a terpolymer of tetrafluoroethylene, hexafluoropropylene, and vinylidene fluoride), PFA (perfluoroalkoxy copolymer resin), ECTFE (ethylene chlorotrifluoroethylene), PVDF (polyvinylidene fluoride), and PEEK (polyether ether ketone). The fluoropolymer membrane may be imbibed or coated with this other material during, prior, or subsequent to retraction. The fluoropolymer (or other material) may also or alternatively be located in at least a portion of or all of the pores of the fluoropolymer membrane.

A further embodiment of the invention takes advantage of a beneficial property of the inventive composite material (i.e., an expanded fluoropolymer membrane having a discontinuous coating of a fluoropolymer thereon). Composite materials of this invention not only exhibit elongation, but also exhibit a dramatic increase in stiffness after achieving a high, optionally predetermined, elongation. As a consequence, the composite materials can be elongated to a point at which further elongation is inhibited by the dramatic increase in stiffness. That is, the composite material has a stop point at which further expansion, elongation, or both occur only in conjunction with a significant increase in pressure or force. Additionally, the composite material is substantially free of wrinkles.

In one specific instance, the inventive composite material can be used to create a covered stent device that requires little pressure to distend to a first diameter but which is highly resistant to further distension after reaching a certain diameter. The result is that the device can be distended in the radial direction under relatively low force until reaching that certain diameter. This diameter is a function of the inventive composite material. In other words, the diametric increase in the diameter of the covered stent device prior to reaching the stop point is a function of the inflection point in the elongation versus force curve for the inventive material, which in turn, is a function of the degree of retraction of the precursor membrane. A benefit of the composite material is that a large increase in diameter of the covered stent device can be achieved prior to reaching the stop point. The stop point of the composite material in exemplary covered stents may occur at a diameter of at least about 7 mm, at least about 8 mm, at least about 9 mm, at least about 10 mm, or even greater. One significance of the stop point is that the stent graft does not itself become aneurismal.

When the composite material is used as a cover for a stent, the composite material remains wrinkle-free and fold-free regardless of the diameter of the covered stent device. For purposes of this invention, the entire device is considered to be "wrinkle-free" if within a 1 cm length of the device, the graft portion is devoid of wrinkles and folds when viewed by the naked eye. It is to be noted that 1 cm length of the device should be used unless the entire length of the device is less than 1 cm. In that instance, the entire device should be utilized to determine if the device is "wrinkle-free." The ability of the cover to remain wrinkle-free results in less or no material infolding during compaction, which, in turn, permits the resulting covered stent device to have a smaller profile (e.g., a reduction in delivery profile of at least about 1 Fr). The absence of folds in the cover reduces or eliminates the potential for thrombus accumulation that can ultimately result in total occlusion of the device. Also, the composite material exhibits high elongation until reaching a length elongation corresponding to an increase in stiffness while substantially retaining the strength properties of the fluoropolymer membrane. The extension of the serpentine fibrils in the composite material to a substantially straight orientation surprisingly retains the strength properties of the fluoropolymer membrane. The composite material allows the cover to be attached to the stent at a small stent diameter and when the stent graft is expanded, the cover does not develop folds. In addition, the composite material both inhibits over-distension of the stent graft and allows over-distension with the application of a substantially higher force. Additionally, the covered stent exhibits minimal foreshortening during the expansion process prior to over-distension.

It is to be appreciated that the break strength of the cover can be altered by using few or numerous layers of the composite material to cover the stent. Alternatively, or in addition to, weaker or stronger fluoropolymer membranes can be used to achieve the same or substantially the same effect.

It is also to be appreciated that when the composite material is used as a cover for a stent, the fluoropolymer coating on the expanded fluoropolymer membrane is not substantially attached to the stent. As used herein, the term "substantially attached" means that the fluoropolymer is not attached to the stent or is only minimally attached to the stent. Rather, the fluoropolymer is utilized as an adhesive to affix two composite materials together to form the cover. For example, a first tube having a fluoropolymer-covered exterior surface and a second tube having a fluoropolymer interior surface are positioned on the interior and exterior surfaces of a stent, respectively, such that the fluoropolymer on the first tube adheres to the fluoropolymer on the second tube (i.e., the opposite surface) through the interstices of the stent, thereby creating a covered stent device. In the present invention, it is important that the composite material forming the cover is not firmly attached to the stent. If the composite material was firmly attached, the cover would tear upon expansion of the covered stent device. That is, the primary means of attachment is achieved by bonding the fluoropolymer (e.g., FEP) portions of the composite covers through the interstices of the stent.

Articles of the present invention can take various forms including, but not limited to, sheets, tubes, covers, and laminates.

Having generally described this invention, a further understanding can be obtained by reference to certain specific examples illustrated below which are provided for purposes of illustration only and are not intended to be all inclusive or limiting unless otherwise specified.

Testing Methods

It should be understood that although certain methods and equipment are described below, any method or equipment determined suitable by one of ordinary skill in the art may be alternatively utilized.

Thickness

Membrane samples were die cut to form rectangular sections about 2.54 cm by about 15.24 cm to measure thickness (using a Käfer Fz1000/30 snap gauge). The average of three measurements was reported.

Scanning Electron Microscopy

Scanning electron micrographs were created choosing magnifications suitable for identifying fibrils. Articles that have been retracted in accordance with the teachings of invention may require elongation in the direction of retraction in order to identify the serpentine fibrils. For the purposes of identifying the number of serpentine fibrils, a field of view of 7 microns by 7 microns of the sample is to be employed.

In addition, for the purpose of characterizing fibril width, measurements should be made for serpentine fibrils that are substantially separated from each other and do not band together or otherwise form series of fibrils paralleling each other within the membrane. To determine the fibril width, a line is drawn through the SEM image to bisect it. The SEM image should be of sufficient magnification such that at least 5 serpentine fibrils and not more than 20 serpentine fibrils are clearly visible within the SEM image. Starting from one edge of the bisected image, the width of the first five consecutive serpentine fibrils that intersect the bisecting line are measured. The measurements are made where the fibril intersects the bisecting line. Next, the five measurements are averaged and the average measurement is recorded.

Radial Elongation Test

The test method that follows describes the test method for an 8 mm covered stent:

A covered stent that had been crushed to its delivery diameter onto an as-packaged (i.e., deflated) 8 mm balloon was positioned on the end of a balloon catheter. The covered stent was placed within the measuring zone of a laser micrometer (e.g., DataMike Model 700, TechMet Co., Dayton, Ohio).

A balloon inflator (e.g., COMPAK balloon inflator, Merit Medical, South Jordan, Utah) was obtained. The balloon inflator was filed with water and attached to the luer fitting of the balloon catheter.

The handle on the inflator was slowly turned while the change in pressure as indicated on the dial was observed. The balloon was then inflated to 2 atmospheres of pressure. The stent easily continued to expand, causing the pressure to drop. The inflation was continued until the pressure of 2 ATM was maintained. The stent was then inflated at 1 ATM intervals and the diameters at those pressures once pressure equilibrated were recorded. Inflation was continued until 14 atmospheres was achieved, which was 1 ATM below the rated burst pressure of the balloon.

A similar procedure should be followed for different sizes of covered stents. For other covered stent sizes, choose an appropriately sized balloon. Continue inflating until reaching 1 ATM below the rated burst pressure of the balloon.

Figure 4:
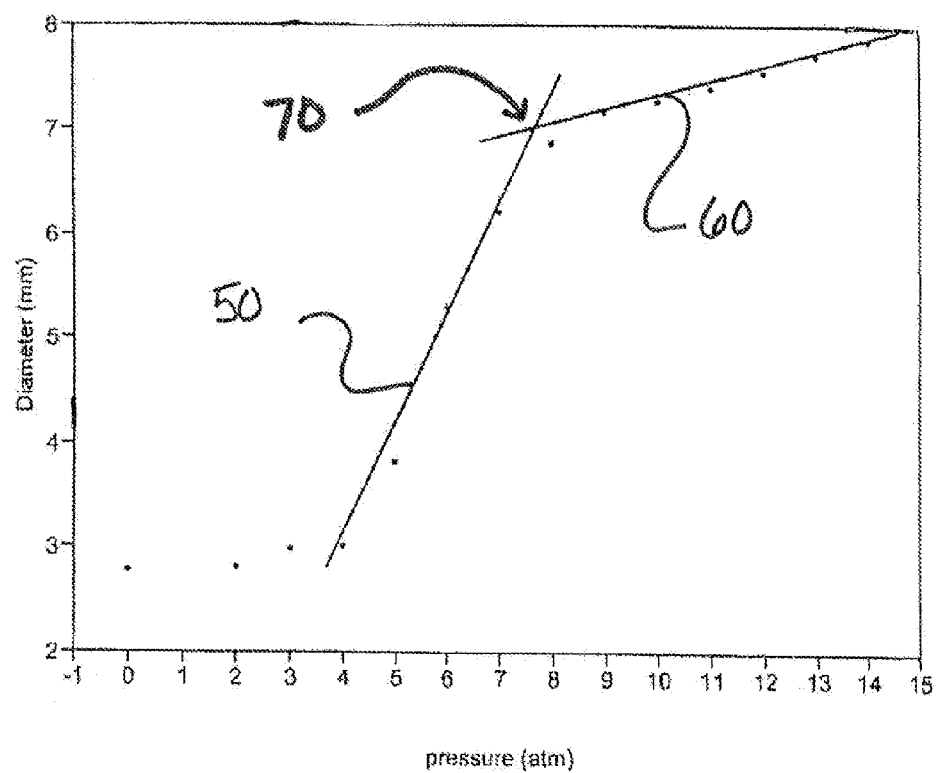
FIG. 4 is a graphical illustration of a pressure vs. diameter curve of an exemplary stent graft according to the present invention where the intersection of the tangent lines depicts the stop point of the composite material.

The pressure-diameter curves relating to composite materials and covered stents of the present invention exhibit an inflection point due to the change in slope upon reaching a diameter referred to herein as the stop point. FIG. 4 is a graphical illustration of a pressure vs. diameter curve of an exemplary stent graft according to the present invention where the intersection of the tangent lines depicts the stop point of the stent graft. The intersection of the tangent lines is depicted by reference numeral 70. An estimate of the stop point may be determined in the following manner. The slope of the pressure-diameter curve prior to reaching the stop point can be approximated by drawing a straight line tangent to the curve as shown as line 50 in FIG. 4. The slope of the pressure diameter curve beyond the stop point can be approximated by drawing a straight line tangent to the curve as shown as line 60 in FIG. 4. The diameter corresponding to the intersection of the two tangent lines is an estimation of the stop point for that composite material.

EXAMPLES

Example 1

Expanded Fluoropolymer Membrane with Discontinuous FEP

Fine powder of PTFE polymer as described and taught in U.S. Pat. No. 6,541,589 was blended with Isopar K (Exxon Mobil Corp., Fairfax, Va.) in the proportion of 0.209 g/g of fine powder. The lubricated powder was compressed into a cylinder to form two pellets that were placed into an oven set at 49° C. for approximately 12 hours. The compressed and heated pellets were ram extruded to produce tape approximately 16.2 cm wide by 0.70 mm thick. The two extruded tapes were then layered and rolled down between compression rolls to a thickness of 0.381 mm. The calendared tape was then transversely stretched to 32 cm (i.e., at a ratio of 2.0:1) and dried at a temperature of approximately 230° C. An approximately 12.5 um thick by approximately 28 cm wide FEP film available from Dupont De Numerous, Inc., (Wilmington, Del.) was obtained. The calendered PTFE tape and the FEP film were laminated together during a longitudinal expansion process that consisted of stretching the two materials, in contact with one another, between banks of rolls over a heated plate set to a temperature of 300° C. The speed ratio between the second bank of rolls to the first bank of rolls was 10:1. The width of the resulting longitudinal expanded membrane was approximately 14 cm. The longitudinally expanded membrane (having FEP film laminated on one side) was then expanded transversely at a temperature of approximately 280° C. to a ratio of about 30:1 and then constrained from shrinkage and heated in an oven set at 360° C. for approximately 10 seconds. The resulting expanded fluoropolymer membrane had regions of FEP discontinuously located on one surface thereof.

This expanded, discontinuously coated fluoropolymer membrane was thermally retracted in the following manner. A roll of precursor membrane where the length direction corresponded with the strongest direction of the membrane, was restrained in the clamps of a heated, uniaxial tenter frame and fed into the heated chamber of the tenter frame. The oven temperature was set to about 270° C. The rails of the tenter frame within the heated chamber were angled inward to allow membrane shrinkage to about 24.6% of its original width in response to the heat. The membrane was retracted over a period of time of approximately 20 seconds.

Figure 2:
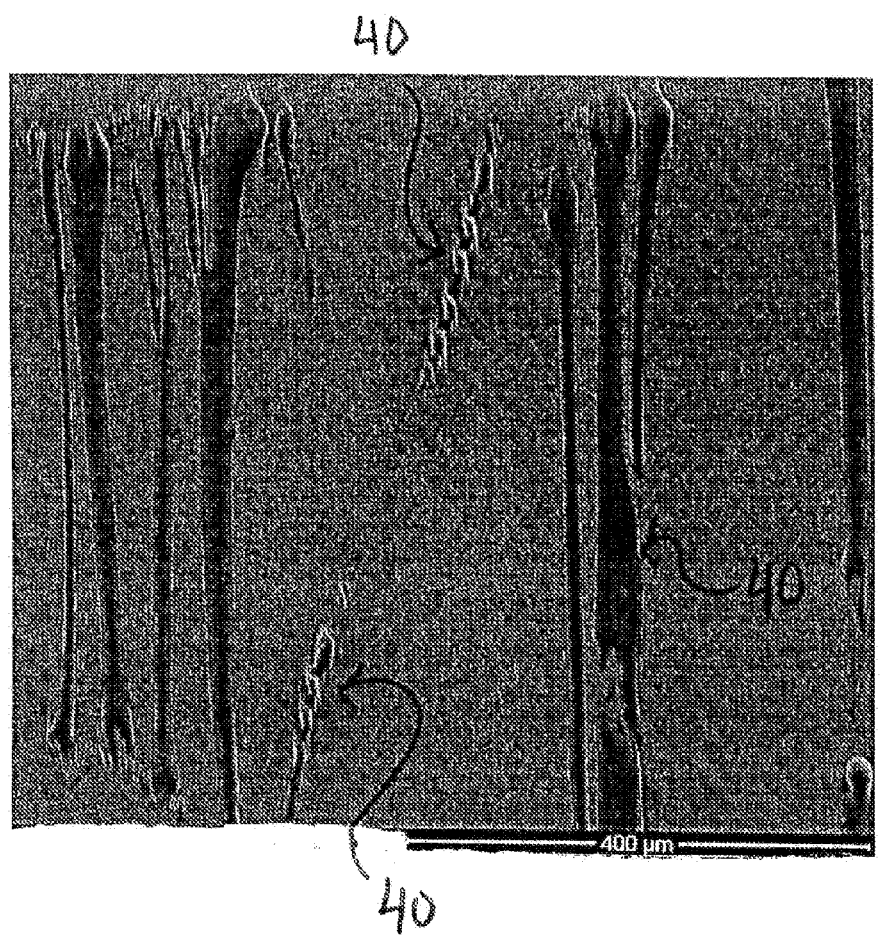
FIG. 2 is a scanning electron micrograph (SEM) of a retracted membrane with a discontinuous coating of FEP taken at 200×.

A scanning electron micrograph of the retracted membrane is provided in FIG. 2, in which the magnification was 200×. Note the presence of regions of FEP, depicted by reference numeral 40, discontinuously located on the surface.

Example 2

The retracted membrane of Example 1 was used to create a covered stent device. An 8 mm diameter×6 mm long stainless steel stent (Cordis Palmaz-Schatz Transhepatic Biliary stent, Cat. No. PS5608A, Lot No. R0599853, Cordis Corp., Bridgewater, N.J.) was obtained. The retracted membrane of Example 1 was used to cover the stent as follows. A tube was constructed from a 150 mm wide sample of the membrane. A 4 mm diameter, 150 mm long stainless steel mandrel was obtained. Twelve layers of the 150 mm wide membrane were circumferentially wrapped around the mandrel such that the retracted direction of the membrane was oriented along the circumferential axis of the mandrel. The FEP side of the membrane faced outward. A soldering iron set to approximately 320° C. was used to spot tack the free edge of the film. A 1.3 cm wide slit of an ePTFE film was wrapped on each end of the tube to avoid longitudinal retraction during subsequent heating. The assembly was then placed into an oven set to 340° C. for about 20 minutes, thereby creating a tube. The tube was allowed to cool and was removed from the mandrel. The tube was cut into two 75 mm lengths. One length was everted in order to position the FEP on the interior surface of the tube.

The tube with the FEP positioned on the exterior surface was placed over the 4 mm stainless steel mandrel. The 8 mm stent was partially inflated to about 3 mm (using the balloon onto which the commercially available stent had been mounted). The stent was removed from the balloon and slipped onto a tapered 4.5 mm stainless steel mandrel in order to increase its diameter. The stent was removed from the 4.5 mm mandrel and slipped on top of the membrane-covered 4 mm stainless steel mandrel. The everted tube was then placed over top of the stent. A 5 mm inner diameter, 0.75 mm thick extruded, expanded sacrificial ePTFE tube was placed over the tube/stent assembly. An iris-style radial crushing device (Blockwise Engineering LLC, Tempe, Ariz.) was used to bring the exterior tube through the stent openings into contact with the inner tube, thereby bringing the FEP on both tubes into contact.

With the tubes still in contact, an ePTFE film was wrapped around the outside of the exterior sacrificial tube. The entire assembly was then placed in an oven set to 320° C. for about 15 minutes. The assembly was removed from the oven, allowed to cool, and the now-formed covered stent was removed from the mandrel and sacrificial layers. The excess tube material at the ends of the stent was trimmed. The covered stent was crushed onto the deflated 8 mm balloon on which the stent had been provided.

Figure 3:
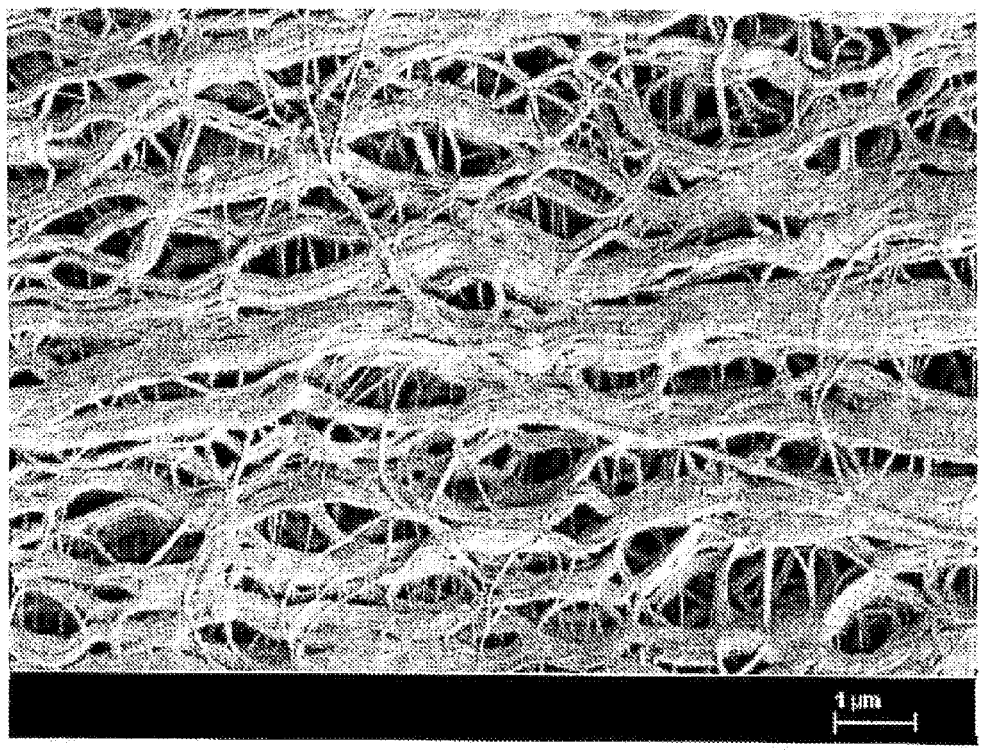
FIG. 3 is a scanning electron micrograph (SEM) of the surface of a stent cover that includes an expanded fluoropolymer membrane having a discontinuous coating of a fluoropolymer thereon where the expanded fluoropolymer membrane includes serpentine fibrils that have a first curve in a first direction, a second curve in a second direction, and a third curve in a third direction taken at 10,000×.

A scanning electron micrograph of the cover inflated to approximately 4 mm is provided in FIG. 3 at a magnification of 10,000×.

A balloon inflator (COMPAK balloon inflator, Merit Medical, South Jordan, Utah)) was obtained and utilized to create a pressure-diameter curve as shown in FIG. 4 using the method described above. FIG. 4 is the pressure-diameter curve corresponding to the covered stent where the cover is formed of the retracted membrane containing discontinuous FEP. As shown in FIG. 4, the retracted membrane can be elongated at a low pressure until reaching the diameter where the slope of the curve substantially decreases, indicating an increased stiffness. The stent cover remained wrinkle-free throughout the test. At about 3 ATM, the stent began to expand. Once about 9 ATM was reached, the stent resisted further expansion due to the presence of the cover. The covered stent exhibited minimal foreshortening during the expansion process and the composite material exhibited a stop point at a diameter of about 7 mm.

The invention of this application has been described above both generically and with regard to specific embodiments. The invention is not otherwise limited, except for the recitation of the claims set forth below.

What is claimed is:

1. An article comprising:
   a wrinkle-free expanded polytetrafluoroethylene membrane having a discontinuous coating of a fluoropolymer material thereon,
   wherein said expanded polytetrafluoroethylene membrane includes a plurality of serpentine fibrils.

2. The article of claim 1, wherein the expanded polytetrafluoroethylene membrane comprises pores and the fluoropolymer material at least partially penetrates a plurality of said pores.

3. The article of claim 1, wherein the fluoropolymer material is fluorinated ethylene propylene.

4. The article of claim 1, wherein the expanded polytetrafluoroethylene membrane has a microstructure of substantially only said serpentine fibrils.

5. The article of claim 1, wherein the expanded polytetrafluoroethylene membrane is thermally retracted in at least one direction to less than about 90% of the initial, expanded polytetrafluoroethylene membrane length.

6. The article of claim 5, wherein the expanded polytetrafluoroethylene membrane is thermally retracted in at least one direction.

7. The article of claim 6, wherein the expanded polytetrafluoroethylene membrane is restrained in at least one direction during said thermal retraction.

8. The article of claim 1, further comprising at least one elastomer incorporated at least partially into the expanded polytetrafluoroethylene membrane.

9. The article of claim 1, wherein said width of said serpentine fibril is 0.5 microns or less.

10. The article of claim 1, wherein said serpentine fibrils have a width of about 1.0 micron or less.

11. The article of claim 1, wherein said serpentine fibrils comprise a multiplicity of fibrils having length portions coalesced together.

12. An endoprosthetic device comprising:
    a wrinkle-free cover defining at least one opening, an interior surface, and an exterior surface, said wrinkle-free cover comprising a composite material including an expanded polytetrafluoroethylene membrane having a discontinuous coating of another material thereon,
    wherein said expanded polytetrafluoroethylene membrane includes a plurality of serpentine fibrils.

13. The endoprosthetic device of claim 12, wherein said serpentine fibrils have a width of about 1.0 micron or less.

14. The endoprosthetic device of claim 13, wherein said serpentine fibrils have a width of 0.5 microns or less.

15. The endoprosthetic device of claim 12, wherein the expanded polytetrafluoroethylene membrane comprises pores and the another material at least partially penetrates a plurality of said pores.

16. The endoprosthetic device of claim 12, wherein said wrinkle-free cover is a cover for a stent.

17. The endoprosthetic device of claim 16, wherein said another material on said exterior surface bonds to said another material on said interior surface through interstices of said stent to affix said wrinkle-free cover to said stent.

18. The endoprosthetic device of claim 12, wherein said another material comprises a member selected from the group consisting of fluorinated ethylene propylene (FEP), ethylene fluorinated ethylene propylene (EFEP), THV (a terpolymer of tetrafluoroethylene, hexafluoropropylene, and vinylidene fluoride), PFA (perfluoroalkoxy copolymer resin), ECTFE (ethylene chlorotrifluoroethylene), PVDF (polyvinylidene fluoride) and PEEK (polyether ether ketone).

19. The endoprosthetic device of claim 12, wherein said another material is fluorinated ethylene propylene.

20. The endoprosthetic device of claim 12, wherein the expanded polytetrafluoroethylene membrane possesses a microstructure of substantially only said serpentine fibrils.

21. The endoprosthetic device of claim 12, wherein said composite material is radially expanded to a diameter beyond which further expansion is inhibited.

22. The endoprosthetic device of claim 12, further comprising at least one elastomer incorporated at least partially into the expanded polytetrafluoroethylene membrane.

23. The endoprosthetic device of claim 12, wherein the expanded polytetrafluoroethylene membrane is thermally retracted in at least one direction to less than about 90% of the initial, expanded polytetrafluoroethylene membrane length.

24. The endoprosthetic device of claim 23, wherein the expanded polytetrafluoroethylene membrane is restrained in at least one direction during said thermal retraction.

25. The endoprosthetic device of claim 12, wherein said composite material exhibits an increase in stiffness when expanded to a diameter of about 7 mm.

26. The article of claim 12, wherein said serpentine fibrils comprise a multiplicity of fibrils having length portions coalesced together.

27. A stent graft comprising:
    a stent having a wall with at least one opening, an exterior surface, and an interior surface; and
    a wrinkle-free cover affixed to said stent,
    wherein said cover comprises a composite material including an expanded polytetrafluoroethylene membrane having serpentine fibrils and a discontinuous coating of a fluoropolymer thereon.

28. The stent graft of claim 27, wherein said composite material at least partially covers at least one of said interior and said exterior surfaces of said stent.

29. The stent graft of claim 27, wherein said serpentine fibrils have a width of about 1.0 micron or less.

30. The stent graft of claim 27, where said cover material remains wrinkle-free regardless of the diameter of the stent graft.

31. The stent graft of claim 27, wherein said composite material is radially expanded to a diameter beyond which further expansion is inhibited.

32. The stent graft of claim 27, wherein said serpentine fibrils comprise a multiplicity of fibrils having length portions coalesced together.

33. The stent graft of claim 27, wherein said expanded polytetrafluoroethylene membrane comprises pores and said fluoropolymer at least partially penetrates a plurality of said pores.

34. The article of claim 27, wherein said fluoropolymer is fluorinated ethylene propylene.

35. The article of claim 27, further comprising at least one elastomer incorporated at least partially into said expanded polytetrafluoroethylene membrane.

\* \* \* \* \*